(12) United States Patent
Murmann et al.

(10) Patent No.: US 12,064,337 B2
(45) Date of Patent: Aug. 20, 2024

(54) DATA-COMPRESSIVE SENSOR ARRAY

(71) Applicant: The Board of Trustees of the Leland Stanford Junior University, Stanford, CA (US)

(72) Inventors: Boris Murmann, Stanford, CA (US); Dante Gabriel Muratore, Palo Alto, CA (US); Eduardo Jose Chichilnisky, Palo Alto, CA (US); Pulkit Tandon, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 804 days.

(21) Appl. No.: 17/284,403

(22) PCT Filed: Oct. 21, 2019

(86) PCT No.: PCT/US2019/057258
§ 371 (c)(1),
(2) Date: Apr. 9, 2021

(87) PCT Pub. No.: WO2020/082081
PCT Pub. Date: Apr. 23, 2020

(65) Prior Publication Data
US 2021/0330449 A1    Oct. 28, 2021

Related U.S. Application Data

(60) Provisional application No. 62/748,432, filed on Oct. 20, 2018, provisional application No. 62/892,510, (Continued)

(51) Int. Cl.
*A61F 2/14*    (2006.01)
*A61N 1/05*    (2006.01)
*G06F 3/01*    (2006.01)

(52) U.S. Cl.
CPC ............ *A61F 2/141* (2013.01); *A61N 1/0543* (2013.01); *G06F 3/01* (2013.01); *A61F 2250/0002* (2013.01)

(58) Field of Classification Search
CPC ............. A61F 2/141; A61F 2250/0002; A61N 1/0543; G06F 3/01; G06F 3/015
See application file for complete search history.

(56) References Cited

U.S. PATENT DOCUMENTS

| 4,461,304 A | 7/1984 | Kuperstein |
|---|---|---|
| 2003/0081134 A1 | 5/2003 | Luo et al. |

(Continued)

FOREIGN PATENT DOCUMENTS

WO    2020082081 A1    4/2020

OTHER PUBLICATIONS

International Preliminary Report on Patentability for International Application PCT/US2019/057258, Report issued Apr. 14, 2021, Mailed Apr. 29, 2021, 5 Pgs.

(Continued)

*Primary Examiner* — Mark W. Bockelman
(74) *Attorney, Agent, or Firm* — KPPB LLP

(57) ABSTRACT

Systems and methods for data-compressive sensing in accordance with embodiments of the invention are illustrated. In one embodiment, a sensor array includes an array of sensor circuitries including a sensor and a comparator. Sensor circuitries in the array are connected via wires which form a series of wired-OR circuits. Readouts can be used to measure the signal on the wires and a decoder in communication with the readouts can be used to resolve signals sensed by particular sensors in the array and their locations.

20 Claims, 12 Drawing Sheets

Related U.S. Application Data filed on Aug. 27, 2019, provisional application No. 62/923,916, filed on Oct. 21, 2019.

(56) References Cited

U.S. PATENT DOCUMENTS

| | | |
|---|---|---|
| 2004/0249302 A1 | 12/2004 | Donoghue et al. |
| 2014/0225760 A1 | 8/2014 | Yang |
| 2022/0168571 A1 | 6/2022 | Shah et al. |

OTHER PUBLICATIONS

International Search Report and Written Opinion for International Application No. PCT/US2019/057258, completed Dec. 12, 2019, Mailed Jan. 3, 2020, 9 Pgs.

Dragas et al., "In Vitro Multi-Functional Microelectrode Array Featuring 59 760 Electrodes, 2048 Electrophysiology Channels, Stimulation, Impedance Measurement, and Neurotransmitter Detection Channels", IEEE Journal of Solid-State Circuits (JSSC), Jun. 2017, 3 pgs.

Frechette et al., "Fidelity of the Ensemble Code for Visual Motion in Primate Retina", Journal of Neurophysiology, vol. 94, No. 1, Jul. 2005, pp. 119-135.

Gabrielli, "Fast Readout Architecture for Large Arrays of Digital Pixels: Examples and Applications", Scientific World Journal, 2014, Published online Mar. 19, 2014, 25 pgs.

Gao et al., "HermesE: A 96-Channel Full Data Rate Direct Neural Interface in 0.13μm CMOS", IEEE Journal of Solid-State Circuits, vol. 47, No. 4, Apr. 2012, pp. 1043-1055.

Karkare et al., "A 75-μW, 16-Channel Neural Spike-Sorting Processor With Unsupervised Clustering", IEEE Journal of Solid-State Circuits, vol. 48, No. 9, Sep. 2013, pp. 2230-2238.

Kleinfelder et al., "A 10000 Frames/s CMOS Digital Pixel Sensor", IEEE Journal of Solid-State Circuits, vol. 36, No. 12, Dec. 2001.

Lebedev et al., "Brain-Machine Interfaces: From Basic Science to Neuroprostheses and Neurorehabilitation", Physiological Review, vol. 97, No. 2, Mar. 2017, pp. 767-837.

Litke et al., "What Does the Eye Tell the Brain?: Development of a System for the Large-Scale Recording of Retinal Output Activity", IEEE Transaction Nuclear Science, vol. 51, No. 4, Aug. 2004, pp. 1434-1440.

Majidzadeh et al., "A 16-Channel, 359 μW, Parallel Neural Recording System Using Walsh-Hadamard Coding", IEEE Custom Integrated Circuits Conference (CICC), Nov. 2013.

Muratore et al., "A Data-Compressive Wired-OR Readout for Massively Parallel Neural Recording", IEEE Transactions on Biomedical Circuits and Systems, vol. 13, No. 6, Dec. 2019, pp. 1128-1140.

Pagin et al., "A Neural Data Lossless Compression Scheme Based on Spatial and Temporal Prediction", IEEE Biomedical Circuits and Systems Conference, Oct. 2017.

Rieseler et al., "A Superposition-Based Analog Data Compression Scheme for Massively-Parallel Neural Recordings", IEEE Biomedical Circuits and Systems Conference, Oct. 2017.

Slutzky, "Brain-Machine Interfaces: Powerful Tools for Clinical Treatment and Neuroscientific Investigations", Neuroscientist, Author manuscript available in PMC Apr. 1, 2020, published in final edited form as Neuroscientist, vol. 25, No. 3, Apr. 2019, pp. 139-154, published online May 17, 2018, doi: 10.1177/1073858418775355.

Tsai et al., "Statistically Reconstructed Multiplexing for Very Dense, High-Channel-Count Acquisition Systems", IEEE Transaction Biomedical Circuits and Systems, vol. 12, No. 1, Feb. 2018. pp. 13-23, DOI: 10.1109/TBCAS.2017.2750484.

Aprile et al., "Adaptive Learning-Based Compressive Sampling for Low-power Wireless Implants", IEEE Transactions on Circuits and Systems I Regular Papers, vol. 65, Jul. 27, 2018, pp. 3929-3941.

Beyeler et al., "Learning to see again: biological constraints on cortical plasticity and the implications for sight restoration technologies", Journal of Neural Engineering, vol. 14, 2017, 19 pgs, doi: 10.1088/1741-2552/aa795e.

Boinagrov et al., "Strength-duration relationship for extracellular neural stimulation: numerical and analytical models", Journal of Neurophysiology, vol. 104, 2010, pp. 2236-2248, doi: 10.1152/jn.00343.2010.

Butterwick et al., "Tissue damage by pulsed electrical stimulation", IEEE Transactions on Biomedical Engineering, vol. 54, No. 12, Dec. 2007, pp. 2261-2267.

Carlson et al., "Continuing progress of spike sorting in the era of big data", Current Opinion in Neurobiology, vol. 55, Apr. 2019, pp. 90-96.

Caspi et al., "Feasibility study of a retinal prosthesis: spatial vision with a 16-electrode implant", Archives of Ophthalmology, vol. 127, No. 4, Apr. 2009, pp. 398-401.

Chader et al., "Artificial vision: needs, functioning, and testing of a retinal electronic prosthesis", Progress in Brain Research, vol. 175, 2009, pp. 317-332.

Chestek et al., "Long-term stability of neural prosthetic control signals from silicon cortical arrays in rhesus macaque motor cortex", Journal of neural engineering, 8(4):045005, Jul. 2011.

Chichilnisky et al., "Functional asymmetries in on and off ganglion cells of primate retina", The Journal of Neuroscience, vol. 22, No. 7, Apr. 1, 2002, pp. 2737-2747.

Christie et al., "Comparison of spike sorting and thresholding of voltage waveforms for intracortical brain-machine interface performance", Journal of Neural Engineering, vol. 12, No. 1, Feb. 2015, doi: 10.1088/1741-2560/12/1/016009.

Chuang et al., "Retinal implants: a systematic review", The British Journal of Ophthalmology, vol. 98, 2008, pp. 852-856.

Chung et al., "A Fully Automated Approach to Spike Sorting", Neuron, vol. 95, Issue 6, Sep. 2017, pp. 1381-1394.

Cogan, "Neural stimulation and recording electrodes", Annual Review of Biomedical Engineering, 2008, vol. 10, pp. 275-309, first published online Apr. 22, 2008, doi: 10.1146/annurev.bioeng.10.061807.160518.

Dayan et al., "Theoretical neuroscience: computational and mathematical modeling of neural systems", MIT Press, 2001, 476 pgs.

De Balthasar et al., "Factors affecting perceptual thresholds in epiretinal prostheses", Investigative Ophthalmology and Visual Science, vol. 49, 2008, pp. 2303-2314.

Devries et al., "Mosaic arrangement of ganglion cell receptive fields in rabbit retina", Journal of Neurophysiology, vol. 78, Issue 4, Oct. 1997, pp. 2048-2060.

Enz et al., "Circuit techniques for reducing the effects of op-amp imperfections: autozeroing, correlated double sampling, and chopper stabilization", Proceedings of the IEEE, Nov. 1996, vol. 84, No. 11, pp. 1584-1614, DOI: 10.1109/5.542410.

Even-Chen et al., "Power-Saving Design Opportunities for Wireless Intracortical Brain Computer Interfaces", Nature Biomedical Engineering vol. 4, No. 10, Oct. 2020, pp. 984-996, Manuscript Available PMC Jul. 19, 2021.

Fan et al., "Epiretinal stimulation with local returns enhances selectivity at cellular resolution", The Journal of Neural Engineering, vol. 16, No. 2, Apr. 2019, 20 pgs.

Field et al., "Functional connectivity in the retina at the resolution of photoreceptors", Nature, vol. 467, No. 7316, Oct. 7, 2010, pp. 673-677.

Fohlmeister et al., "Modeling the repetitive firing of retinal ganglion cells", Brain Research, vol. 510, Issue 2, Mar. 5, 1990, pp. 343-345.

Fraser et al., "Control of a brain-computer interface without spike sorting", Journal of Neural Engineering, vol. 6, No. 5, Oct. 2009, doi: 10.1088/1741-2560/6/5/055004.

Goetz et al., "Electronic Approaches to Restoration of Sight", Reports on progress in physics, institute of physics publishing, Bristol, GB, Aug. 9, 2016, vol. 79, No. 9, p. 96701, XP020307763, ISSN: 0034-4885, DOI: 10.1088/0034-4885/79/9/096701.

Gollisch et al., "Eye smarter than scientists believed: neural computations in circuits of the retina", Neuron, vol. 65, No. 2, Jan. 2010, pp. 150-164.

Grifantini, "Aiding the Eye, Watching the Brain: James Weiland,IEEE Fellow, explores the unique challenges of retinal prostheses", IEEE Pulse, vol. 8, 2017, pp. 39-41.

(56) References Cited

OTHER PUBLICATIONS

Grosberg et al., "Activation of ganglion cells and axon bundles using epiretinal electrical stimulation", Journal Neurophysiology, vol. 118, No. 3, Sep. 1, 2017, pp. 1457-1471, doi: 10.1152/jn.00750. 2016.

Harrison et al., "Wireless Neural Recording with Single Low-Power Integrated Circuit", IEEE Transactions on Biomedical Engineering, vol. 54, No. 6, Aug. 2009, pp. 322-329.

Horsager et al., "Predicting visual sensitivity in retinal prosthesis patients", Investigative Ophthalmology and Visual Science, vol. 50, 2009, pp. 1483-1491.

Huang et al., "A 200 nV offset 6.5 nV//spl radic/Hz noise PSD 5.6 kHz chopper instrumentation amplifier in 1 /spl mu/m digital CMOS", 2001 IEEE International Solid-State Circuits Conference, Feb. 2001.

Humayun et al., "The Bionic Eye: A Quarter Century of Retinal Prosthesis Research and Development", Ophthalmology, vol. 123, 2016, pp. S89-S97.

Irwin et al., "Enabling Low-Power, Multi-Modal Neural Interfaces Through a Common, Low-Bandwidth Feature Space", IEEE Transactions on Neural Systems and Rehabilitation Engineering, vol. 24, No. 5, May 2016, pp. 521-531.

Jensen et al., "Thresholds for activation of rabbit retinal ganglion cells with an ultrafine, extracellular microelectrode", Investigative Ophthalmology & Visual Science, vol. 44, No. 8, Aug. 2003, pp. 3533-3543, doi: 10.1167/iovs.02-1041.

Jepson et al., "Focal electrical stimulation of major ganglion cell types in the primate retina for the design of visual prostheses", Journal of Neuroscience, vol. 33, No. 17, Apr. 24, 2013, pp. 7194-7205.

Jepson et al., "High-fidelity reproduction of spatiotemporal visual signals for retinal prosthesis", Neuron, vol. 83, Jul. 2014, pp. 87-92.

Jepson et al., "Spatially Patterned Electrical Stimulation to Enhance Resolution of Retinal Prostheses", The Journal of Neuroscience, vol. 34, No. 14, Apr. 2014, pp. 4871-4881.

Jung et al., "Active confocal imaging for visual prostheses", Vision Research, vol. 111, 2014, pp. 182-196.

Li et al., "Sums of Spike Waveform Features for Motor Decoding", Frontiers in Neuroscience, vol. 11, No. 406, Jul. 18, 2017, doi: 10.3389/fnins.2017.00406.

Lorach et al., "Photovoltaic restoration of sight with high visual acuity", Nature Medicine, vol. 21, 2015, pp. 476-482.

Marblestone et al., "Physical Principles for Scalable Neural Recording", Frontiers in Computational Neuroscience, vol. 7, No. 137, 2013, 49 pgs.

Merrill et al., "Electrical stimulation of excitable tissue: design of efficacious and safe protocols", Journal of Neuroscience Methods, vol. 141, 2005, pp. 171-198.

Nanduri et al., "Retinal prosthesis phosphene shape analysis", 2008 30th Annual International Conference of the IEEE Engineering in Medicine and Biology Society, 2008, pp. 1785-1788.

Okazawa et al., "A Time-Domain Analog Spatial Compressed Sensing Encoder for MultiChannel Neural Recording", Sensors, vol. 18, No. 1, Jan. 2018, 21 pgs.

Rey et al., "Past, present and future of spike sorting techniques.", Brain Research Bulletin, vol. 119, 2015, pp. 106-117.

Rhoades et al., "Unusual Physiological Properties of Smooth Monostratified Ganglion Cell Types in Primate Retina.", Neuron, vol. 103, No. 4, Aug. 21, 2019, pp. 658-672.e6.

Richard et al., "Recognizing retinal ganglion cells in the dark. In: Advances in Neural Information Processing Systems", Stanford Medicine, 2015, pp. 2476-2484.

Roska et al., "The retina dissects the visual scene into distinct features", The New Visual Neurosciences, 2014, pp. 163-182.

Sekirnjak et al., "High-resolution electrical stimulation of primate retina for epiretinal implant design", Journal of Neuroscience, vol. 28, No. 17, Apr. 23, 2008, pp. 4446-4456.

Shah et al., "Efficient characterization of electrically evoked responses for neural interfaces", Neural Information Processing Systems (NeurIPS), 2019.

Shah et al., "Optimization of Electrical Stimulation for a High-Fidelity Artificial Retina", 2019 9th International IEEE/EMBS Conference on Neural Engineering (NER), IEEE, Mar. 20, 2019, pp. 714-718, XP033551652, DOI: 10.1109/NER.2019.8716987.

Sharma et al., "Acquisition of Neural Action Potentials Using Rapid Multiplexing Directly at the Electrodes", Micromachines, doi: 10.3390/mi9100477, 2018.

Shlens et al., "The structure of multi-neuron firing patterns in primate retina", The Journal of Neuroscience, vol. 26, No. 32, Aug. 9, 2006, pp. 8254-8266, doi: 10.1523/JNEUROSCI.1282-06.2006.

Sodagar et al., "A fully integrated mixed-signal neural processor for implantable multichannel cortical recording", IEEE Transactions on Bio-Medical Engineering, vol. 54, No. 6, Jun. 2007, pp. 1075-1088, doi: 10.1109/TBME.2007.894986.

Takahashi et al., "A 1/2.7-in 2.96 MPixel CMOS Image Sensor With Double CDS Architecture for Full High-Definition Camcorders", IEEE Journal of Solid-State Circuits, vol. 42, No. 12, Jan. 2008, pp. 2960-2967.

Trautmann et al., "Accurate Estimation of Neural Population Dynamics Without Spike Sorting", Neuron, vol. 103, No. 2, Jul. 17, 2019, 42 pgs.

Wu et al., "Deep compressive autoencoder for action potential compression in large-scale neural recording", Journal of Neural Engineering, vol. 15, No. 6, Dec. 2018, 20 pgs.

Yh-L et al., "A review and update on the current status of retinal prostheses (bionic eye)", British Medical Bulletin, vol. 109, 2014, pp. 31-44.

Zhou et al., "Toward true closed-loop neuromodulation: artifact-free recording during stimulation", Current Opinion in Neurobiology, vol. 50, 2018, pp. 119-127.

Zrenner et al., "Subretinal electronic chips allow blind patients to read letters and combine them to words", Proceedings of the Royal Society B: Biological Sciences, vol. 278, 2011, pp. 1489-1497.

DATA-COMPRESSIVE SENSOR ARRAY

CROSS-REFERENCE TO RELATED APPLICATIONS

The current application is a U.S. national stage application of PCT Application No. PCT/US2019/057258 entitled "Data-Compressive Sensor Array" filed Oct. 21, 2019, which claims the benefit of and priority under 35 U.S.C. § 119(e) to U.S. Provisional Patent Application No. 62/748,432 entitled "Distributed Analog-to-Digital-Converter for Data-Compressive Readout of Sensor Arrays with Sparse Signal Activity" filed Oct. 20, 2018, U.S. Provisional Patent Application No. 62/892,510 entitled "Data-Compressive Wired-OR Readout for Massively Parallel Neural Recording" filed Aug. 27, 2019, and U.S. Provisional Patent Application No. 62/923,916 entitled "Artificial Retina" filed Oct. 21, 2019. The disclosures of U.S. Provisional Patent Application Nos. 62/748,432, 62/892,510 and 62/923,916 are hereby incorporated by reference in its entirety for all purposes.

FIELD OF THE INVENTION

The present invention generally relates to data-compressive sensor arrays and, more specifically, data-compressive wired-OR readout electrode arrays for neural recording.

BACKGROUND

Neurons (nerve cells) are cells that carry electrical impulses throughout the body. The electrical impulses (action potentials, or "spikes") can encode various biological messages between different parts of the body. Sensory and control information is conveyed and processed using these electrical impulses as part of the nervous system. These electrical impulses can be detected and measured using sensors such as, but not limited to electrodes.

The human eye is made of numerous different types of cells. One type of cell is the retinal ganglion cells (RGCs), which can be further broken down into many subtypes. Generally, RGCs are neurons located near the inner surface of the retina of the eye, which receive visual information from photoreceptor cells and convey the visual information to the brain.

SUMMARY OF THE INVENTION

Systems and methods for data-compressive sensing in accordance with embodiments of the invention are illustrated. One embodiment includes a data-compressive sensor array including a ramp signal generator configured to distribute a global ramp signal, an array of sensor circuitries, where the sensor circuitries in the array are arranged in a plurality of rows and a plurality of columns, and where each sensor circuitry includes a sensor, and a comparator configured to compare the global ramp signal to a signal produced by the sensor, where the comparator for each sensor circuitry in a given row in the plurality of rows is connected via a given row wire, where the comparator for each sensor circuitry in a given column in the plurality of columns is connected via a given column wire, and where each row wire and each column wire form a wired-OR circuit, a row readout configured to sense the signal on each row wire, a column readout configured to sense the signal on each column wire, and a decoder connected to the row readout and the column readout configured to provide signal data describing signals produced by the sensors using a pulse-position modulation scheme.

In another embodiment, the data-compressive sensor array includes a Gray counter in communication with the decoder.

In a further embodiment, the decoder is configured to disregard signals from the column readout and signals from the row readout that describe collision events.

In still another embodiment, the decoder is configured to estimate signals sensed by sensors in the array which are involved in a collision event by using a baseline value.

In a still further embodiment, the baseline value is estimated using a 3-tap non-causal finite impulse response filter.

In yet another embodiment, the decoder is a probabilistic decoder.

In a yet further embodiment, the data-compressive sensor array is part of a brain-computer interface.

In another additional embodiment, the brain-computer interface is an artificial sight prosthetic.

In a further additional embodiment, the artificial sight prosthetic is a dictionary-based artificial sight prosthetic.

In another embodiment again, the data-compressive sensor array is implanted proximal to the retinal ganglion cell layer of an eye.

In a further embodiment again, the signal data provided by the decoder is used to estimate a receptive field mosaic.

In still yet another embodiment, the receptive field mosaic is estimated by performing spike sorting on the signal data provided by the decoder, and classifying retinal ganglion cells in the retinal ganglion cell layer based on the spike sorting.

In a still yet further embodiment, wherein the sensors are electrodes, and the electrodes are directed to stimulate cells in order to trigger the impression of sight.

In still another additional embodiment, the data-compressive sensor array includes a transmitter capable of transmitting signal data provided by the decoder.

In a still further additional embodiment, the transmitter is a wireless transmitter.

In still another embodiment again, the data-compressive sensor array includes a receiver capable of receiving control data.

In a still further embodiment again, the receiver is a wireless receiver.

In yet another additional embodiment, a method for data-compressive sensing, including connecting a plurality of sensor circuitries in an array having a plurality of rows and a plurality of columns, where each sensor circuitry includes a sensor, and a comparator configured to compare a global ramp signal to a signal produced by the sensor, where the comparator for each sensor circuitry in a given row in the plurality of rows is connected via a given row wire, where the comparator for each sensor circuitry in a given column in the plurality of column is connected via a given column wire, and where each row wire and each column wire form a wired-OR circuit, sensing the state of each row wire using a row readout, sensing the state of each column wire using a column readout, and decoding the states received from the row readout and the column readout to provide signal data describing the signals produced by the sensors using a decoder implementing a pulse-position modulation scheme.

In a yet further additional embodiment, the plurality of sensor circuitries are implanted into the retinal ganglion cell layer of an eye.

In yet another embodiment again, the method is performed by an artificial sight prosthetic.

In a yet further embodiment again, the method includes estimating a receptive field mosaic based on the signal data.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

Figure 1:
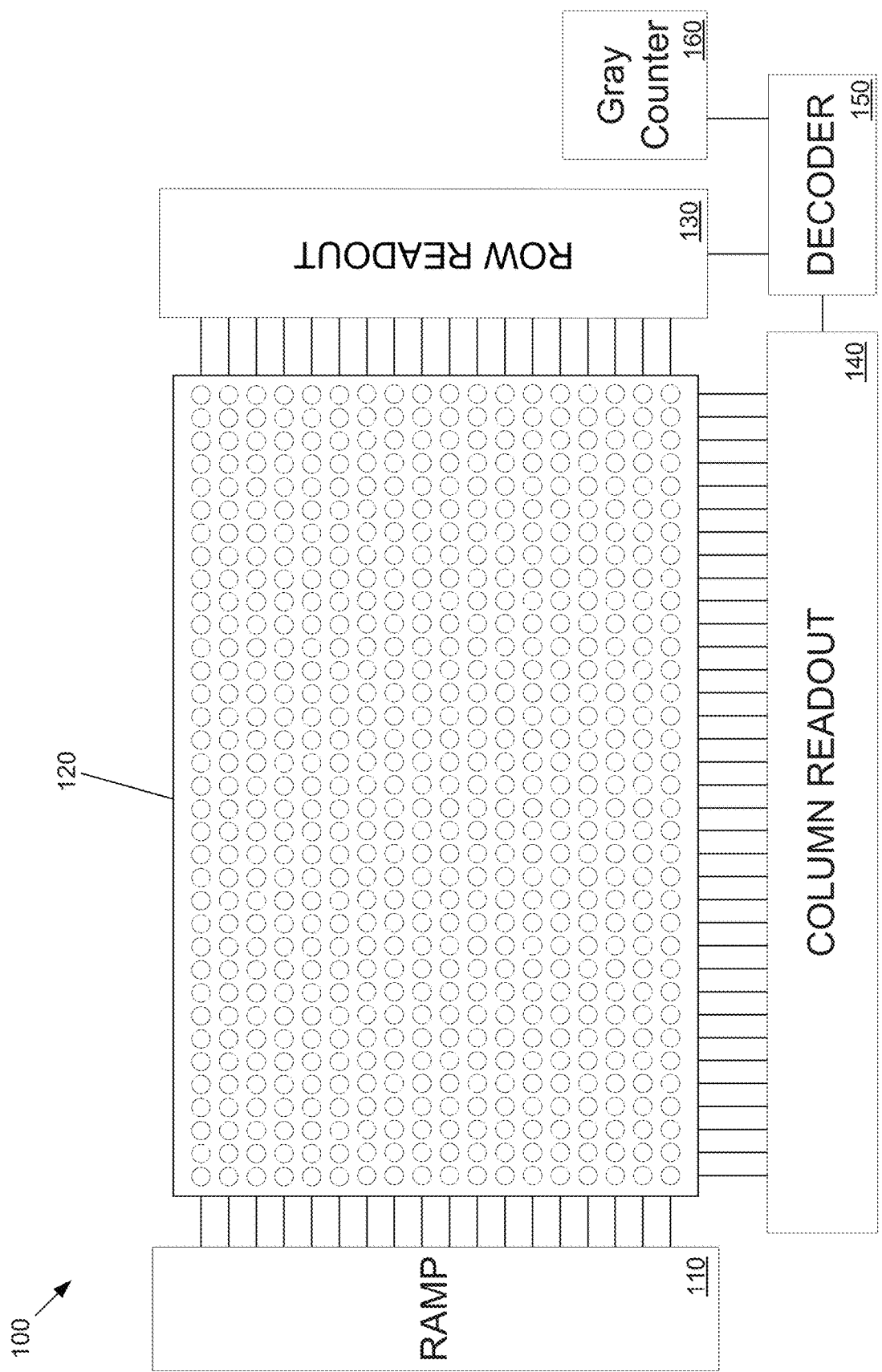
FIG. 1 is a block diagram illustrating a data-compressive sensor array in accordance with an embodiment of the invention.

Turning now to the drawings, data-compressive sensor arrays are described. Brain-computer interfaces (BCIs, also referred to as brain-machine interfaces (BMIs)) are devices which can record neural activity and/or stimulate neurons in order to provoke a desired response. In numerous embodiments, recorded neural activity is processed by the BCI to produce a desired effect by the user. BCIs are an emerging clinical technology that can also have non-clinical uses. Common clinical applications of interest include, but are not limited to, control of prosthetic limbs, vocalization of thoughts, and restoration of sight. However, many other applications, clinical or otherwise, are possible using BCI technology.

One hurdle to BCI technology is the limitations placed on their properties due to the delicate nature of organic tissue. For example, as BCIs often include implanted electrodes and/or other physical interfacing methods between machine and neuron, there are restrictions upon how much heat can be generated proximal to the tissue without causing damage. Further, depending on the location of the BCI, there may be significant physical size restrictions due to the need of maintaining the integrity of surrounding tissue. These restrictions can impede not only local processing capabilities, but also data transfer rates as transmission methodologies must also conform to the physical limitations of the BCI implantation site.

Both of these limitations and/or more can come into play in many different types of BCI. For illustrative purposes, the below will focus on BCIs designed for ocular implantation with the goal of restoring vision, however the systems and methods described herein can be applied to any number of different BCI types and implantation locations, as well as non-BCI related devices that require data-compressive readouts from dense sensor arrays. The average human retina is made of over one million individual nerve cells which send signals through the optic nerve that, when processed by the human brain, produce a coherent mental representation of the visual environment. The eye is not only a delicate organ that is space restrictive and heat sensitive, but it also has a tendency to move within its socket causing potential interference in wireless data links. Due to the aforementioned heat tolerances, there is an incentive to offload computationally intensive processing to outside of the eye. In turn, this means that data received from and transmitted to the interface with the neurons within the eye must quickly and reliably be transmitted outside of the eye to provide substantially real-time vision. Systems and methods for ocular BCIs as well as a discussion of the various restrictions can be found in U.S. Provisional Application No. 62/821,763 titled "Systems and Methods for Dictionary-Based Artificial Sight Prosthetics" the disclosure of which is hereby incorporated by reference in its entirety. A discussion of underlying principles of data-compressive sensor arrays is found below.

Principles of Data-Compressive Sensor Arrays

While data-compressive sensor arrays described herein can be utilized in any of a number of different contexts, they are particularly suited to use in BCI and neural signal processing contexts. As such, the below principles will be discussed with particular reference to biological systems. However, one of ordinary skill in the art would appreciate that the circuitry described herein can be easily modified to match non-biological applications.

Conventionally, BCIs use circuitries that record local field potentials, i.e. low frequency signals that result from the aggregated activity of many neurons (on the order of at least hundreds). However, in many situations, a higher resolution of measurement would be beneficial. With a high resolution of measurement such as on the order of single to tens of cells, individual cells can be identified which in turn can lead to more precise stimulation. One process of identifying individual cells involves recording action potentials ("spikes") from individual cells and digitally processing the signals to identify and separate the spikes originating in different cells in a process referred to as "spike sorting." Cell type identification can then performed on the basis of neural response properties to differentiate neurons encoding different types of information. In order to support clinical and scientific goals, it is desirable for BCIs to be able to support parallel recording from a large number of different electrodes in order to enhance resolution and/or neuron coverage. However, as mentioned above, there are significant engineering challenges to the recording process. Assuming 100,000 channels and a heat dissipation limit of 10 mW, the per channel power budget is only 100 nW. Further, even if it was possible for an analog-to-digital interface to fit within this budget, at an average sampling rate of 20 kilosamples per second (kS/s), where each sample is 10 bits, the 100,000 channel array would need to be able to move 20 Gb/s. Due to these limitations, modern large-scale electrode arrays tend to use only a small number of channels at a time for recording.

While various attempts have been made to address this issue, there are problems with currently proposed designs. For example, in applications that require only binary spike train information, large power and data reductions are achievable using on-chip thresholding. However, this precludes off-chip spike sorting and cell type identification. To achieve data reduction without sacrificing such information, on-chip spike sorting and compression have been considered, but do not alleviate the issues with massive multiplexing and digitization on the frontend. Some methodologies attempt to improve efficiency of active analog multiplexing but do not address the massive amount of data generated post-digitization. Finally, while a technique in which both multiplexing and compression occur simultaneously via analog channel superposition has been proposed by Rieseler et al. in "A Superposition-Based Analog Data Compression Scheme for Massively-Parallel Neural Recordings", 2017 *IEEE Biomedical Circuits and Systems Conference*, October 2017, the scalability of this approach is limited by the noise summation of the superimposed channels.

Generally, spike sorting and cell type identification rely on recorded voltage waveforms produced by spikes and measured by electrodes. The waveforms that exceed a threshold voltage can be identified and projected into a low-dimensional subspace for clustering of waveforms arising from different neurons. However, in many embodiments, because the rate of spikes emitted by neurons (between approximately 1 and 200 Hz) is relatively low compared to the sampling frequency utilized to capture the spike waveforms (on the order of tens of kS/s), and because each spike is very brief (approximately 1 ms), the circuitry described herein can digitize only the samples that are important for reconstructing the spike waveform. In a variety of embodiments, this leads to a high compression rate.

While it is difficult to formulate an exact criterion for selecting the input samples that are most useful for spike sorting, in many embodiments, it can be approximated based on the conjecture that samples outside the baseline noise window ($\pm k \times \sigma_n$, where k is a design-mediated constant and $\sigma_n$ is the noise standard deviation) are important for spike sorting. Samples outside of the baseline noise window are referred to herein as "spike samples" versus the remaining "baseline samples." In numerous embodiments, while there may be samples belonging to a true spike within the baseline noise window, it can be assumed that they are not required for spike sorting given the larger spike samples.

Following the above convention, channels carrying a spike sample are referred to as "spike channels" and channels carrying a baseline sample are referred to as "baseline channels." In numerous embodiments, the same channel can be a spike channel for one time sample, and a baseline channel at a different time sample. Due to time sparsity in the neural activity, at any given time, it is likely that the number of spike channels is small. Moreover, in a variety of embodiments, for a given sample time, the probability of multiple spike channels having the same digital code after analog-to-digital conversion is low. Conversely, in many embodiments, the probability of multiple spike channels having the same digital code after analog-to-digital conversion is high for baseline channels. However, depending on the sensed environment, these probabilities may shift. This dichotomy is referred to as "amplitude diversity" within spike channels. In many embodiments, amplitude diversity can be leveraged to integrate multiplexing and compression within a data-compressive array circuitry without expending extra compute energy to separate baseline samples from spike samples.

To address the above limitations while maintaining sufficient functionality and efficiency, data-compressive sensor arrays can perform lossy compression in the mixed-signal domain (i.e. before full-digitization) by exploiting two principles. First, as noted above, in many scenarios spikes are sparse in space and time. Therefore, recording only spikes and not voltage samples between spikes is sufficient. Second, it is often only necessary to distinguish spikes produced by different cells, and therefore it is not necessary that spike waveforms be perfectly recorded. Circuitries that can leverage these principles are discussed in further detail below.

Data-Compressive Sensor Arrays

As discussed above, data-compressive sensor arrays can integrate multiplexing and compression within a single circuitry. In numerous embodiments, this is achieved by creating a circuit in which the digitized voltage on a given sensor is retained only if it is different from the values on other sensors. In many embodiments, this is achieved efficiently using a linear search digital-to-analog (DAC) converter coupled with a wired-OR readout. In this scheme, for each channel and each input sample, the linear search DAC indicates the input voltage with a brief pulse at a discreet time step proportional to the quantized voltage (the number of distinct time step sets of the DAC resolution). At each time step, the outputs of the different sensors can be combined with an OR logic across the rows and across the columns. Consequently, in a variety of embodiments, if only a single sensor produces a pulse (i.e. it is the only sensor producing a quantized voltage corresponding to the current time step), then the electrode location is indicated by a unique row and column. On the other hand, if multiple pulses from different sensors occur at the same time steps (i.e., the quantized voltages on many sensors are equal), multiple rows and columns are activated and no unique sensor is indicated. In this way, the data-compressive sensor array can retain only the uniquely identified sensors. In many embodiments, data-compressive sensor arrays include transmitters and/or receivers capable of transmitting and receiving data such as, but not limited to, sensed signals and/or control data used to configure and/or command the data-compressive sensor array's operation with regards to stimulation and/or recording processes.

Turning now to FIG. 1, a high level block-diagram for a data-compressive sensor array in accordance with an embodiment of the invention is illustrated. Data-compressive sensor array 100 includes a ramp DAC 110. The ramp DAC drives a globally distributed period ramp signal across an array of sensor circuits 120. Sensor circuits include a sensor and circuitry for processing a sensed signal. The processing circuitry is discussed in further detail below with respect to FIG. 2. In numerous embodiments, the sensors are electrodes, although the sensors can be any kind of sensor as appropriate to the requirements of specific applications of embodiments of the invention.

In a variety of embodiments, each sensor circuit in the array is located on a single vertical wire and a single horizontal wire. For example, in numerous embodiments, a sensor array with 256 horizontal wires and 256 vertical wires, a total of 65,536 sensor circuits would be distributed such that each horizontal wire and each vertical wire would have 256 sensor circuits connected. However, these numbers are merely exemplary, and any number of different wires and sensor circuits can be utilized as appropriate to the requirements of specific applications of embodiments of the invention, such as, but not limited to, those with unequal number of horizontal and vertical wires (e.g. rectangular arrays), arbitrarily shaped arrays (e.g. non-rectangular), with more or fewer sensor circuits. In some embodiments, different areas of the array may have more or fewer sensor circuits than other areas of the array. In a variety of embodiments, sensor circuitries can be arbitrarily connected and/or disconnected from a particular wire.

Each sensor circuitry pushes its output along the connected horizontal and vertical wires. The horizontal wire states are sensed by a row readout 130 and vertical wire states are sensed by a column readout 140 at each ramp value. The wire states are passed to a decoder 150. Decoders can convert the pulse position modulated signals into a digital signal reflecting the signal detected by the sensors. In a variety of embodiments, decoders can be configured to only digitize spike samples and disregard baseline samples. In many embodiments, decoders only digitize signals that meet a predetermined certainty threshold. In numerous embodiments, a Gray counter 160 can be used as part of the digitization process.

Figure 2:
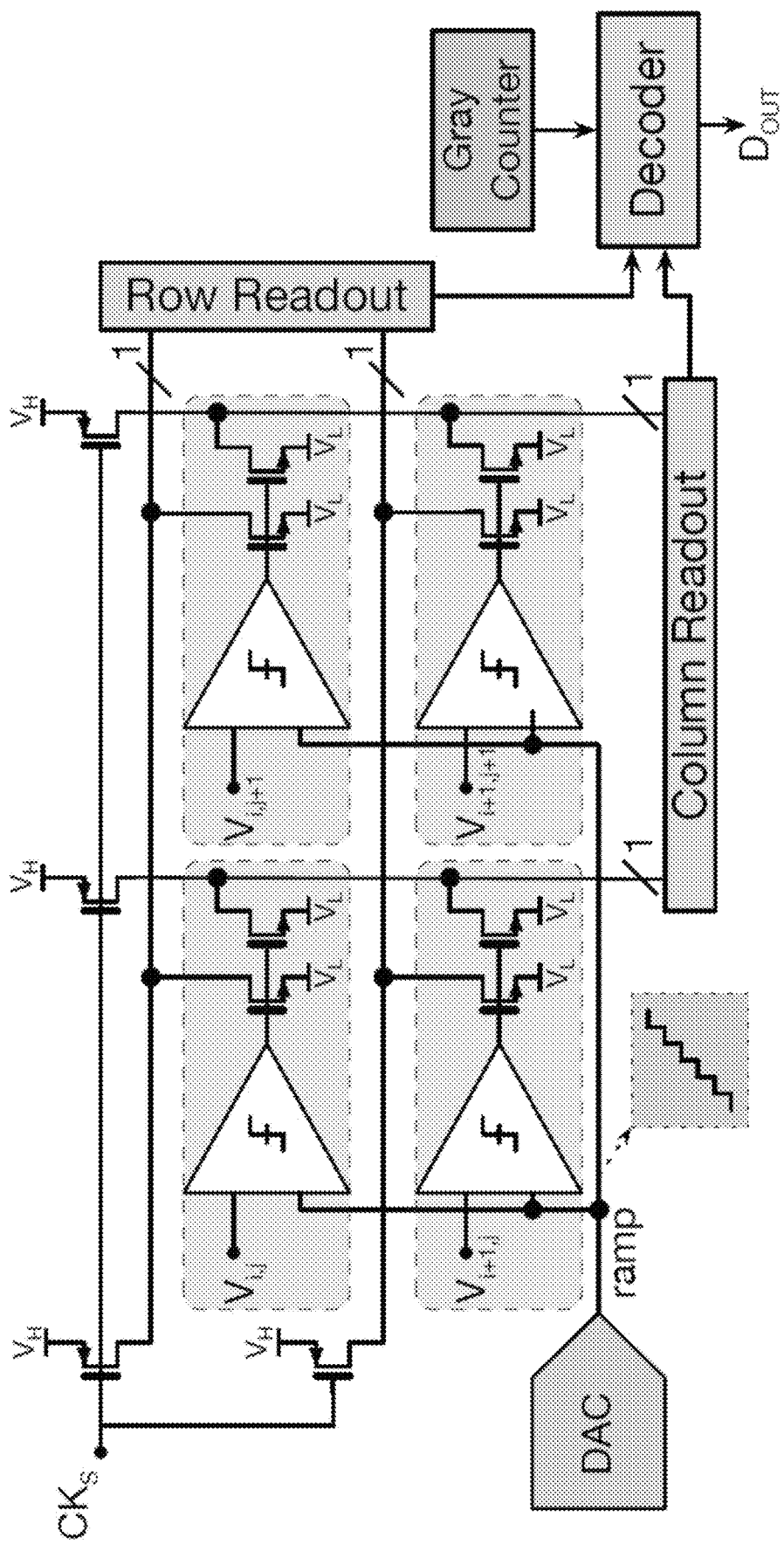
FIG. 2 is a circuit diagram illustrating a data compressive sensor array in accordance with an embodiment of the invention.
Figure 3:
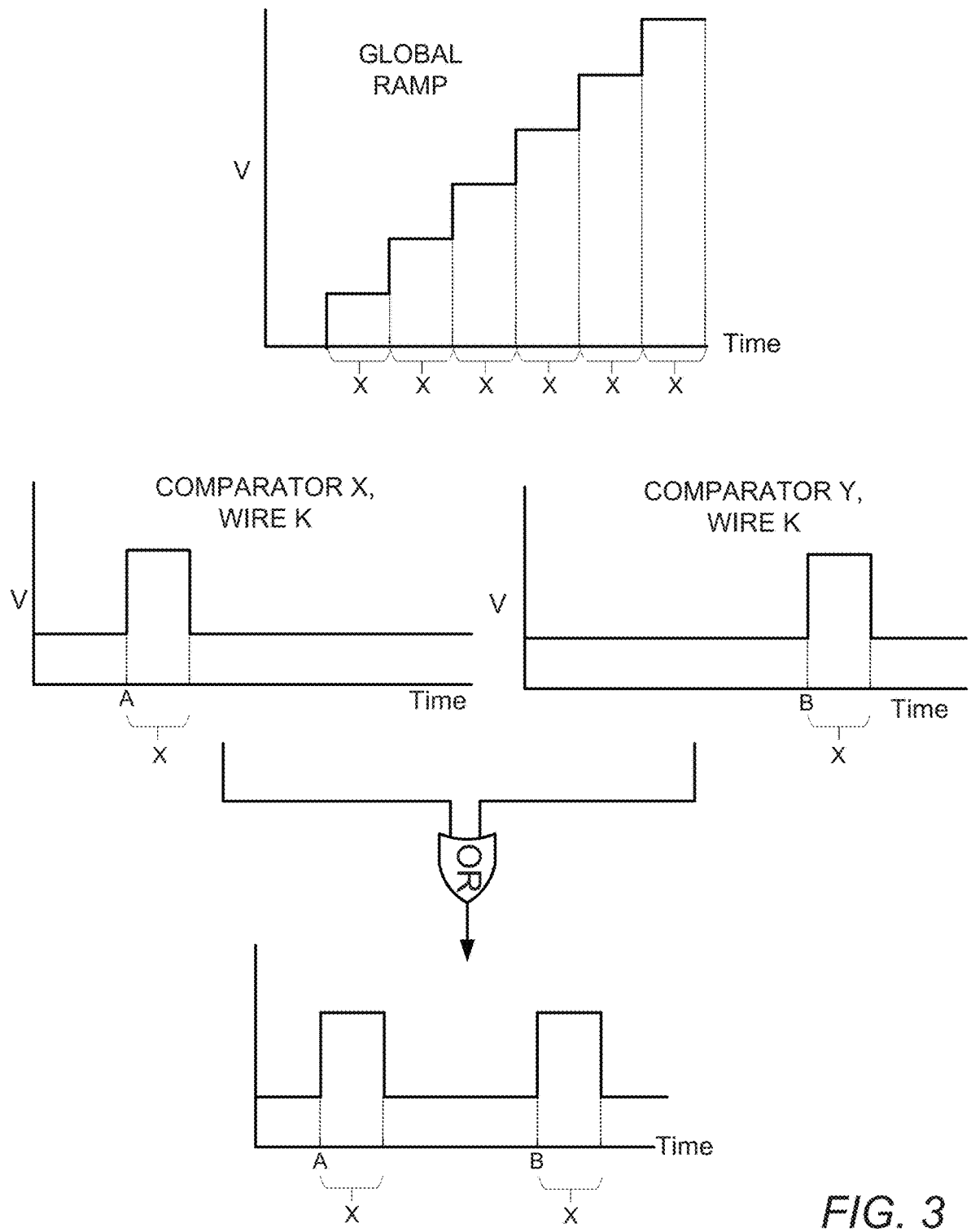
FIG. 3 is an illustration of two signals being fed through a wired-OR connection in accordance with an embodiment of the invention.

Turning now to FIG. 2, a detailed view of an example data-compressive sensor array having four sensor circuits in a 2×2 arrangement in accordance with an embodiment of the invention is illustrated. In the illustrated architecture, the digitization of the spike signals is based on the single slope analog to digital conversion principle. The ramp signal is globally distributed to each sensor circuitry, and each sensor circuit contains a voltage comparator fed by the ramp and the sensor. Each comparator output is provided to the horizontal wire and vertical wire associated with the coordinate of the respective sensor circuitry. In this way, the vertical and horizontal wires across the array function as wired-OR circuits such that each row readout and each column readout senses a pulse position modulated signal reflecting unique amplitudes recorded by any sensor circuitry on the particular row or column, respectively, for a particular ramp cycle. This is illustrated in accordance with an embodiment of the invention in FIG. 3. A first pulse from a first comparator and a second, later pulse from a second comparator connected to the same wire will combine when subject to the wired-OR operation. By matching the states of horizontal and vertical wires, in many situations, which comparators have triggered can be accurately determined. Further, in numerous embodiments, the amplitude of the sensed signal is encoded by the pulse position corresponding to the ramp signal.

While particular architectures are illustrated with respect to FIGS. 1 and 2, one of ordinary skill in the art can appreciate that modifications can be made without departing from the scope and spirit of the invention. For example, depending on the sensors used and/or the environment being sensed, different array sizes might be utilized, ramp signals may be varied to better match the signals being sensed, more than one wire per row and/or column may be used, and/or any other number of modifications can be made as appropriate to the requirements of specific applications of embodiments of the invention. In numerous embodiments, wires can be in arbitrary patterns such as, but not limited to, a diagonal arrangement, a zig-zag arrangement, a circular arrangement, and/or any other arrangement as appropriate to the requirements of specific applications of embodiments of the invention. In a variety of embodiments, sensor circuitries can be reassigned to different wires based on a control signal. In many embodiments, multiple different sensor circuitry/wire configurations can be stored. In numerous embodiments, configurations can be conveyed and/or switched between in response to commands carried as control data. As noted, it is evident there are cases where is cannot be easily identified what sensor circuit in the array generated a particular signal. For example, when multiple comparators are triggered at the same time, it is difficult or impossible to determine the location of the triggered comparators. These "collision" scenarios are discussed in more detail below.

Collisions

In many situations, more than one comparator may trigger at the same time point for a given ramp value. In numerous embodiments, this causes a situation where there is no unique decoding enabling absolute localization. An instance of this scenario is referred to as a "collision." While it may initially appear that collisions are an inherent flaw in the design as information is lost, they are in fact advantageous in many applications. In numerous embodiments, data compression can be achieved by maximizing collision events for baseline samples and minimizing collision events for spike samples. In various embodiments, collision events are maximized as long as spike sorting performance requirements are met. As such, in some scenarios, spike channels can be discarded. In many embodiments, the probability and severity of a collision depends on the signal distribution of the signal being sensed. In neural signal sensing applications, the neural signal tends to spend most of its time near the baseline, and thus massive collisions are likely for ramp values around zero, which also do not correspond to particularly useful information (i.e., no spike activity).

In a variety of embodiments, the above architecture performs better when the offset between channels is small with respect to the quantization step. In many embodiments, a wider signal probability mass function caused by the offset can increase the collision rate for spike samples. In numerous embodiments, performance is not significantly impacted so long as the offset standard deviation is kept below 10 $\mu V_{rms}$. In many embodiments, a residual offset of this magnitude or smaller is achievable using techniques such as, but not limited to, chopping and correlated double sampling.

Figure 4:
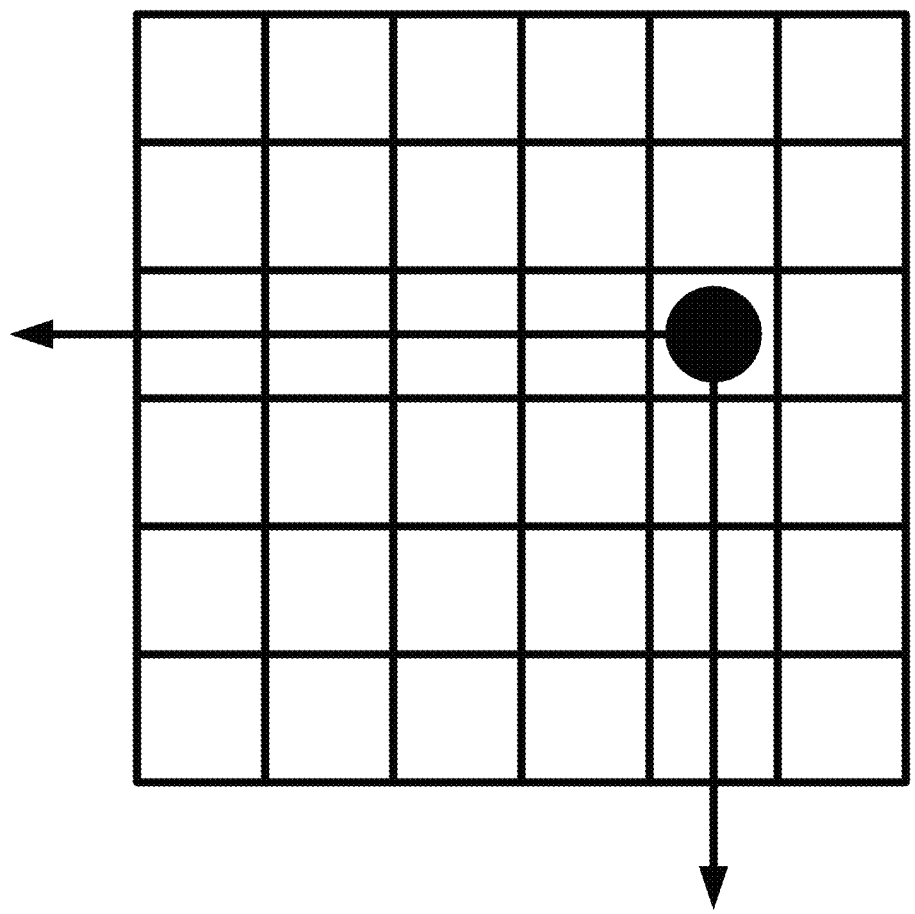
FIG. 4 is a conceptual illustration of a "no collisions" state in accordance with an embodiment of the invention.

In many embodiments, a "no collision" scenario is when only one comparator within the array triggers for a given ramp value, and therefore the location of the triggered comparator can be uniquely determined by matching the values from the vertical and horizontal readouts and the sample can be assigned to a particular sensor in the array. An example of a "no collision" scenario in accordance with an embodiment of the invention is illustrated in FIG. 4. At the particular time illustrated, only one comparator has triggered a pulse on the wire. Because of this, only the particular horizontal wire and vertical wire connected to the sensor circuitry will carry the particular pulse produced by the firing comparator, and thus the originating sensor circuitry can be identified by the decoder by matching the column and row readout values.

Figure 5:
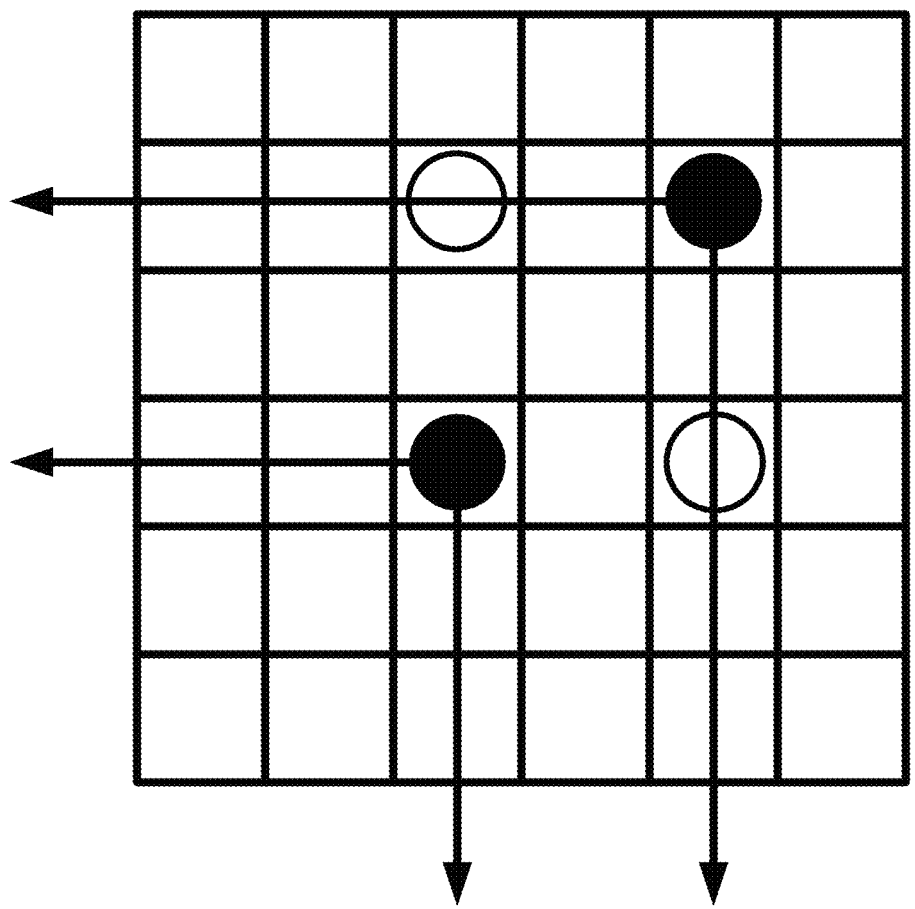
FIG. 5 is a conceptual illustration of a "minor collisions" state in accordance with an embodiment of the invention.
Figure 6:
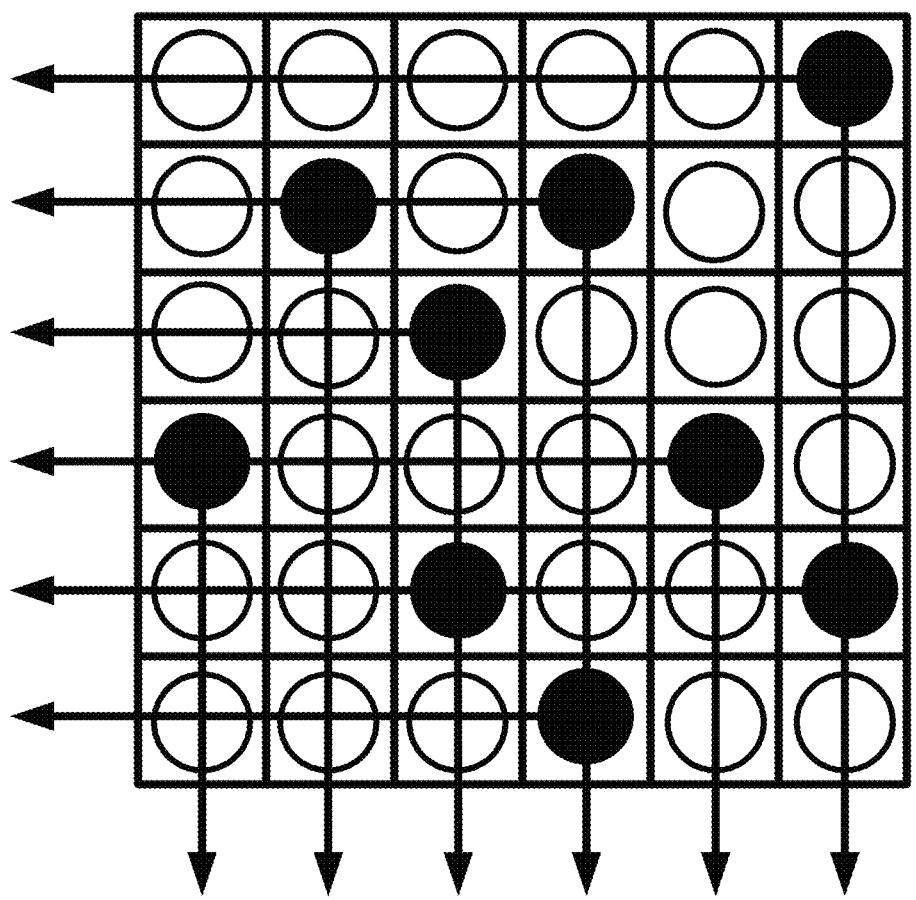
FIG. 6 is a conceptual illustration of a "massive collisions" state in accordance with an embodiment of the invention.
Figure 7:
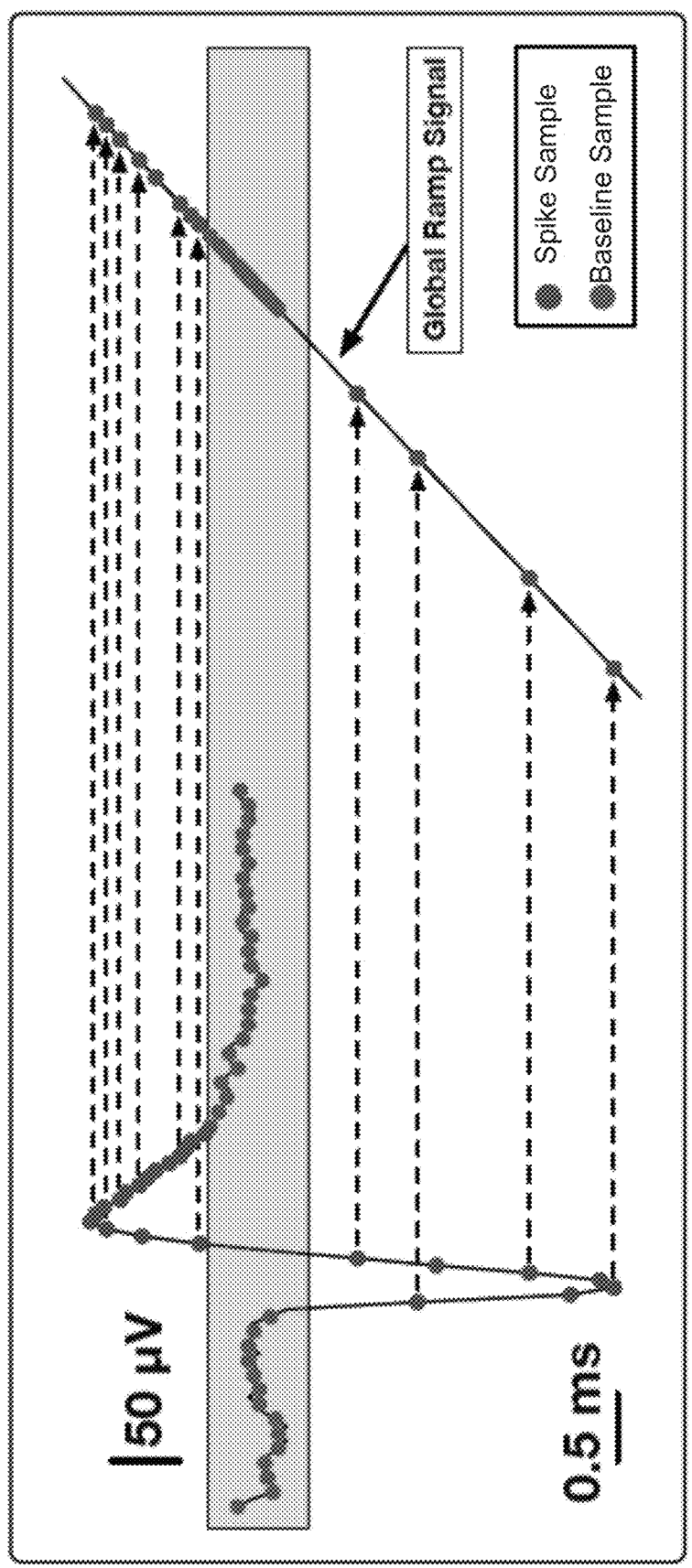
FIG. 7 is a chart illustrating samples taken using a data-compressive sensor array in accordance with an embodiment of the invention.

In numerous embodiments, the degree to which collisions occur can be distinguished as "small collisions," in which a few channels are activated together, and "massive collisions," in which many channels are activated together. An example of a "small collision" in accordance with an embodiment of the invention is illustrated in FIG. 5. The shaded circles represent actual triggered comparators. The unshaded circles represent locations that, if the comparators were triggered at those locations instead, would lead to the same values on the respective wires. Similarly, an example of a "massive collision" in accordance with an embodiment of the invention is illustrated in FIG. 6. In the illustrated scenario, it is impossible to detect any unique triggered comparators. Collisions can be visualized in other ways as well. For example, a projection of samples onto the ramp signal in accordance with an embodiment of the invention is illustrated in FIG. 7. The ramp signal is globally distributed to the sensor circuitries in the array as discussed above. Each circle reflects a triggered comparator. As illustrated, spike samples reflect unique samples identified in no-collision scenarios and are located away from the central cluster of baseline samples reflecting a massive collision scenario (i.e. a large number of comparators were triggered at approximately the same ramp value). Viewed another way, the central cluster reflects the baseline sensed value by the sensors, which in the illustrated embodiment is the average voltage of an RGC.

As illustrated, values around the average, baseline voltage of the neural signal will be recorded the majority of the time. Given a large number of neurons, most sensors across the array will be sensing the baseline voltage, and therefore will all trigger their respective comparators at approximately the same point during the ramp. These baseline samples can then be disregarded. In contrast, points along the spike will be moved away from the baseline, and therefore are much more likely to trigger a comparator when the ramp is outside of the baseline range.

Decoders can take the measurements taken by the row and column readouts and use them to reconstruct the spikes sensed at any arbitrary point in the array. Decoding strategies are discussed in more detail below.

Spike Decoding

Depending on the requirements of specific applications of embodiments of the invention, decoders can handle collisions in any of a variety of ways. For example, in many embodiments, a naïve decoder approach includes using only collision-free samples to reconstruct the spike waveforms and discards all other data. As discussed above, spike samples are almost always recovered and baseline samples make up the majority of discarded data. Consequently, missing samples can initially be set to zero and subsequently reconstructed using a 3-tap non-causal finite impulse response (FIR) filter.

Figure 8:
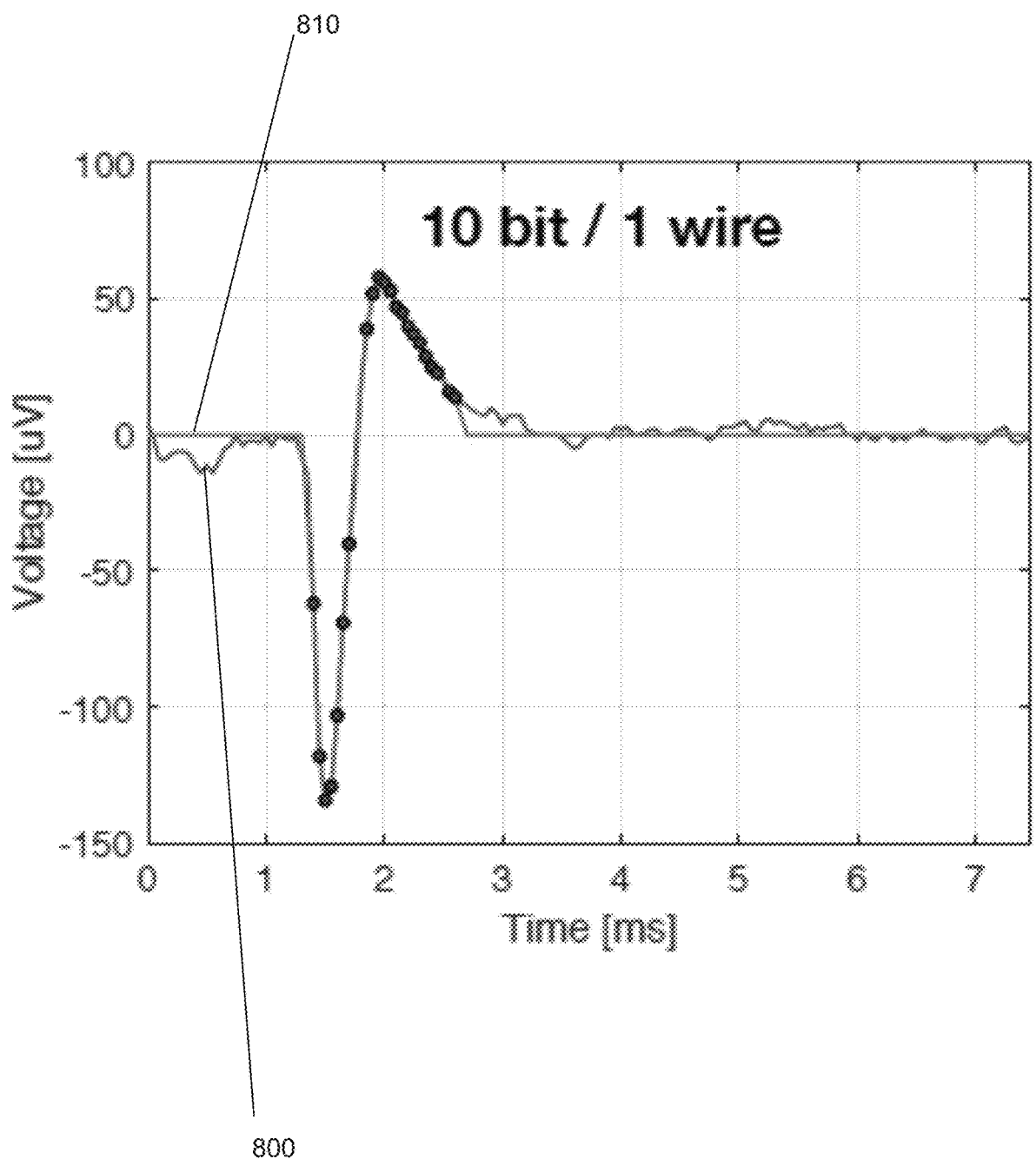
FIG. 8 is a chart illustrating the reconstruction of a neural signal using a data compressive sensor array in accordance with an embodiment of the invention.

For the particular case of interfacing with RGCs, the coefficients of the filter can be set to $b_{-1}=0.5$, $b_0=0$, and $b_{+1}=0.5$. However, the coefficients can be easily modified depending on the nature of the signals being sensed. An illustration of this decoding process in accordance with an embodiment of the invention is illustrated in FIG. 8. Signal 800 is the ground truth signal being sensed for illustrative purposes. Signal 810 is the reconstructed signal using the FIR filter. As shown, the ground truth signal can be accurately approximated using only spike samples (shaded circles). In many embodiments, compression is achieved by outputting only the address of the collision-free channels and reconstructing the data off-chip. In this way, computation can be shifted off board, for example to an area with fewer physical constraints. However, depending on the requirements of specific applications of embodiments of the invention, the signals can be reconstructed in the decoder connected to the array.

Figure 9:
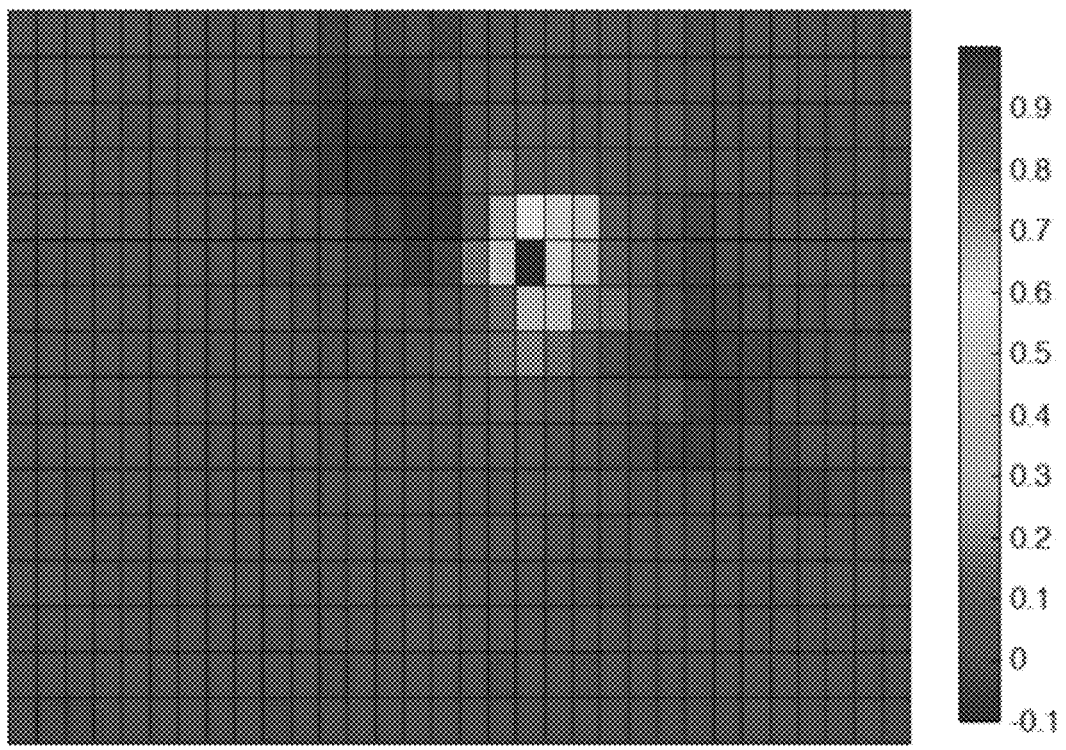
FIG. 9 is a correlation matrix in accordance with an embodiment of the invention.

Beyond the amplitude distribution of a spike, an important metric of neural signals is their spatial correlation. In many situations, nearby neurons are more likely to spike at approximately the same time. A graphical representation of this in the form of a correlation matrix for a particular channel (in this case, channel (6,19)) in accordance with an embodiment of the invention is illustrated in FIG. 9. Correlation is maximum at channel (6,19), and decreases as a function of distance from (6,19), illustrating that signals recorded in nearby channels are often correlated.

Figure 10:
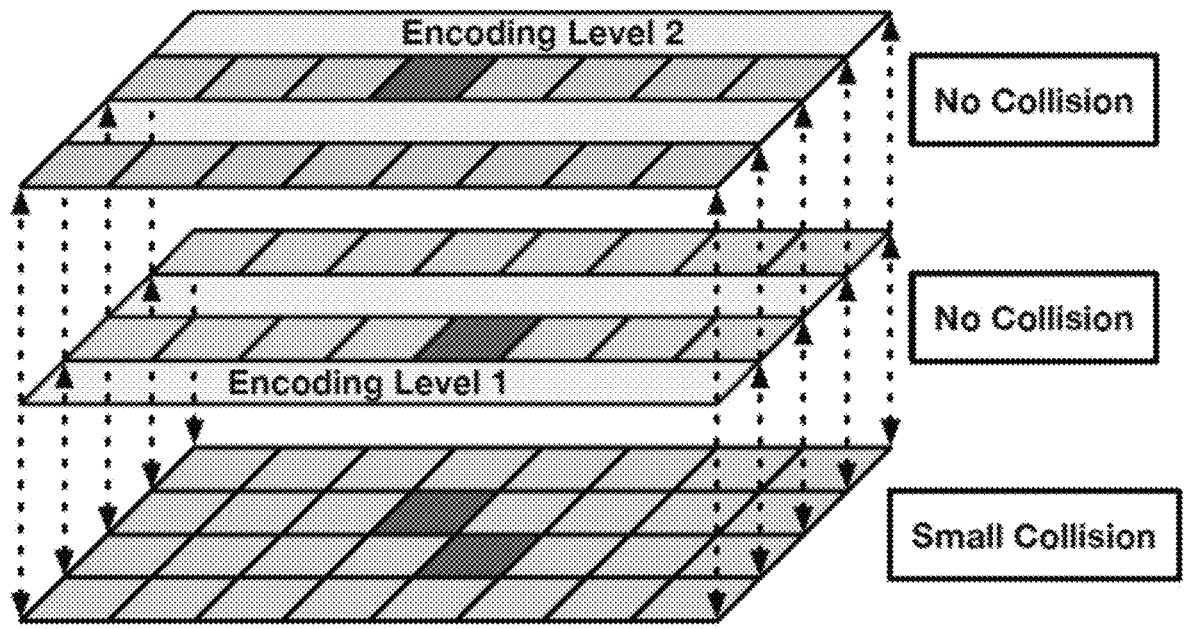
FIG. 10 illustrates a two-wire encoding scheme in accordance with an embodiment of the invention.

In some embodiments, this phenomenon is accounted for by encoding comparator outputs onto different row and column wires for adjacent channels. The incurred cost of extra digital wires is generally minimal so long as the wire count is kept significantly smaller than the number of sensor circuits. Effectively, multiple wires per row/column split the array into multiple sub-arrays generating multiple encoding levels. An example of multiple encoding levels in accordance with an embodiment of the invention is illustrated in FIG. 10. The first and second encoding levels do not have collisions as the diagonally adjacent triggered comparators are connected to different wires. While a single wire scheme would result in a small collision, said collision is avoided by having multiple wires. While a two-wire scheme is illustrated in FIG. 10, any number of different wires can be utilized as appropriate to the requirements of specific applications of embodiments of the invention.

While adding additional wires can reduce collision rates and waveform distortion, it can also impact the data compression rate. The tradeoffs can be analyzed using the following equation:

$$R = \left\lceil \log_2\left(\frac{N_{row}}{W}\right) + \log_2(N_{col}) \right\rceil \alpha_{cf,W} f_s$$

where R is the data rate, $N_{row}$ and $N_{col}$ are the number of rows and columns in the array, W is the number of wires per row/column, $\alpha_{cf}$ is the rate of collision-free channels per sample, $\alpha_{cf,W} > \alpha_{cf}$ (for W>1) is the total rate of collision free-channels per sample, and fs is the sampling frequency. In numerous embodiments, the channels are connected to the additional wires such that rows are interleaved in the encoding strategy. Consequently, in such cases, rows can be addressed with only $$\left\lceil \log_2\left(\frac{N_{row}}{W}\right) \right\rceil$$

bits.

In numerous embodiments, a probabilistic decoding process can be implemented that can utilize collision data to improve reconstruction. In a variety of embodiments, spatial and amplitude continuity of neural signals can be used to resolve collisions, although depending on the environment, probabilistic decoders can be constructing using situation specific principles. An example probabilistic decoder can maintain a prior probability matrix $P \in \mathbb{R}^{N_{row} \times N_{col}}$ over the whole array at each time sample. In many embodiments, If a spike is received at a particular sensor, it's surrounding sensors will present a similar amplitude with high probability, leading to a potential collision. A heuristic algorithm can capture this effect by increasing the prior matrix P by a hyper-parameter $P_{inc}$ for all the collision-free channels and the ones adjacent to it. The prior P for all the other channels can be decreased by another hyper-parameter $P_{dec}$ to signify receding activity from these channels.

If a small collision occurs at a particular ramp-step, the heuristic algorithm can chose the $r_{firing}$ (another-hyperparameter) channels with the higher prior value P, and thus resolve the collision by choosing the most-likely channels to carry that signal value. A collision can be defined as small if the number of rows (and/or columns) activated is less than a hyper-parameter c. In numerous embodiments, to help the heuristic algorithm resolve collisions effectively, the decoder can process the signal from the lowest ramp value to zero and then from the highest ramp value to zero, so that the prior matrix is first setup with collision-free cases before resolving collision cases.

While various decoding strategies are discussed above, any number of different encoding strategies can be utilized as appropriate to the requirements of specific applications of embodiments of the invention. Depending on the type of environment and the signals to be sensed, the decoder can be modified to adapt to the received signal without departing from the scope and spirit of the invention. As the circuit architecture described herein can be used to measure and record neuron activation with high rates of compression, circuits described herein are particularly suited to BCI applications. A discussion of decoding RGC firing patterns is discussed below.

Retinal Prosthesis

Figure 11:
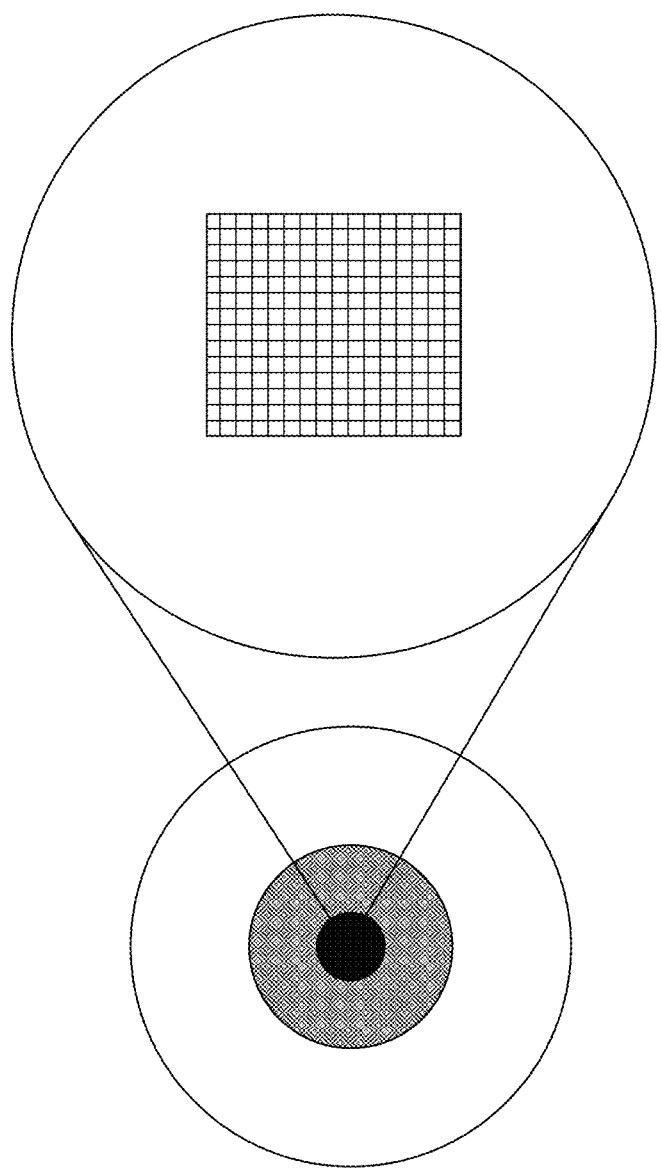
FIG. 11 conceptually illustrates a data-compressive sensor array connected to the retinal ganglion cell layer of an eye in accordance with an embodiment of the invention.

In a variety of embodiments, a data-compressive sensor array is implanted as part of a retinal prosthetic. Retinal prosthetics can be used to restore vision in some individuals by triggering RGC activation in a way that mimics how they would normally function in a functional visual system. In many embodiments, the data-compressive sensor array is implanted proximal to the RGCs as illustrated in accordance with an embodiment of the invention in FIG. 11. To understand the idiosyncrasies and/or which neurons an implanted data-compressive sensor array is adjacent to, the recording functionalities described above can be used. However, it is important to note that in numerous embodiments, data-compressive sensor arrays can further be utilized to selectively trigger neuron activation via stimulation electrodes. In numerous embodiments, the stimulus electrode is the same as a sensor implemented as a sensing electrode. In a variety of embodiments, commands to stimulate RGCs are conveyed by control data.

Neurons can be classified into cell types based on their temporal response properties and their receptive fields. In many embodiments, visual receptive fields are calculated by correlating images focused on the retina with the spiking activity of the neuron. In numerous embodiments, the receptive fields of a single cell type form a mosaic that covers the entire recorded region of the retina. In a variety of embodiments, this information is utilized to compile dictionaries for dictionary-based artificial sight prosthetics.

Figure 12:
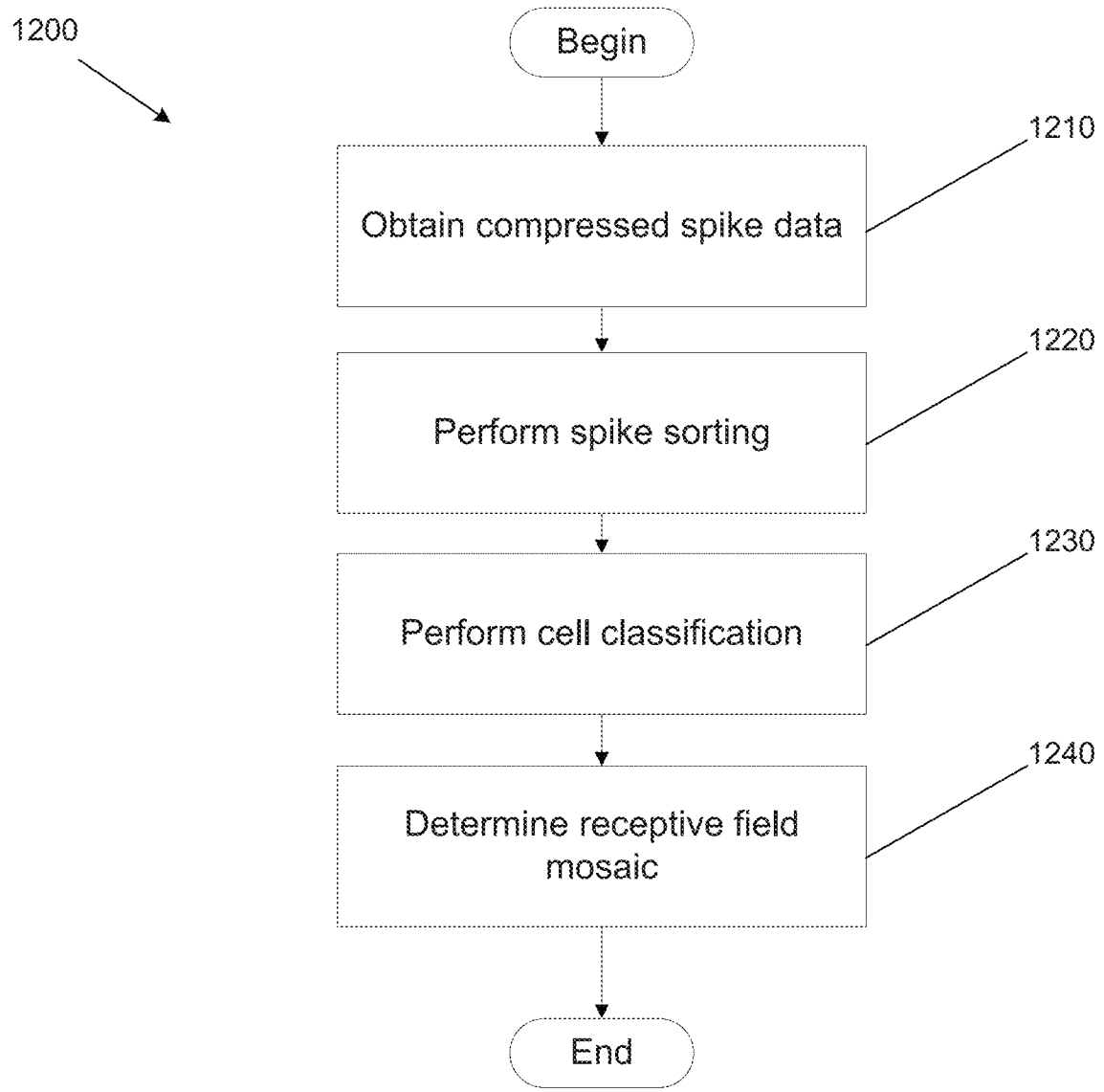
FIG. 12 is a flow chart illustrating a process for determining receptive field mosaics using data from a data-compressive sensor array in accordance with an embodiment of the invention.

Turning now to FIG. 12, a method for determining receptive field mosaics in accordance with an embodiment of the invention is illustrated. Process 1200 includes obtaining (1210) compressed spike data from a data-compressive sensor array. Spike sorting is performed (1220) on the spikes defined by the spike data. In many embodiments, spike sorting includes locating spikes in the raw spike data by per-channel signal thresholding, where the threshold is set at the $N_{th}$ times the standard deviation of the given channel. Second, principal components analysis is performed on the raw spike waveforms, and spikes are then projected onto the first five principal components and clustered using an expectation-maximization algorithm. Finally, the spike sorter removes neurons that exhibit refractory period violations or unusually low firing rates. However, any number of different spike sort implementations can be utilized including those that utilize different numbers of principal components, different thresholds, other outlier removal criteria, and/or any other implementation as appropriate to the requirements of specific applications of embodiments of the invention.

Process 1200 further includes performing (1230) cell classification. In many embodiments, cell classification is performed using measured receptive field properties of identified neurons. In numerous embodiments, this process can be accelerated by matching unclassified neurons with known, ground-truth classified neurons based on their temporal response properties and receptive fields. Classified cells can then be used to determine (1240) the receptive field mosaic for each cell type.

While a specific method for generating receptive field mosaics using the data from a data-compressive sensor array is discussed above with respect to FIG. 12, any of a number of different methods can be utilized as appropriate to the requirements of specific applications of embodiments of the invention. Further, data-compressive sensor arrays are not restricted to only acquiring data for generating receptive field mosaics, and have many different applications and functional environments. Although specific data-compressive sensor arrays are discussed above, any number of different architectures can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A data-compressive sensor array, comprising:
   a ramp signal generator configured to distribute a global ramp signal;
   an array of sensor circuitries, where the sensor circuitries in the array are arranged in a plurality of rows and a plurality of columns, and where each sensor circuitry comprises:
   a sensor; and
   a comparator configured to compare the global ramp signal to a signal produced by the sensor;
   where the comparator for each sensor circuitry in a given row in the plurality of rows is connected via a given row wire;
   where the comparator for each sensor circuitry in a given column in the plurality of columns is connected via a given column wire; and
   where each row wire and each column wire form a wired-OR circuit;
   a row readout configured to sense the signal on each row wire;
   a column readout configured to sense the signal on each column wire; and
   a decoder connected to the row readout and the column readout configured to provide signal data describing signals produced by the sensors using a pulse-position modulation scheme.

2. The data-compressive sensor array of claim 1, further comprising a Gray counter in communication with the decoder.

3. The data-compressive sensor array of claim 1, wherein the decoder is configured to disregard signals from the column readout and signals from the row readout that describe collision events.

4. The data-compressive sensor array of claim 3, wherein the decoder is configured to estimate signals sensed by sensors in the array which are involved in a collision event by using a baseline value.

5. The data-compressive sensor array of claim 4, wherein the baseline value is estimated using a 3-tap non-causal finite impulse response filter.

6. The data-compressive sensor array of claim 1, where the data-compressive sensor array is part of a brain-computer interface.

7. The data-compressive sensor array of claim 6, wherein the brain-computer interface is an artificial sight prosthetic.

8. The data-compressive sensor array of claim 7, wherein the artificial sight prosthetic is a dictionary-based artificial sight prosthetic.

9. The data-compressive sensor array of claim 7, wherein the data-compressive sensor array is implanted proximal to the retinal ganglion cell layer of an eye.

10. The data-compressive sensor array of claim 9, wherein the signal data provided by the decoder is used to estimate a receptive field mosaic.

11. The data-compressive sensor array of claim 10, wherein the receptive field mosaic is estimated by:
    performing spike sorting on the signal data provided by the decoder; and
    classifying retinal ganglion cells in the retinal ganglion cell layer based on the spike sorting.

12. The data-compressive sensor array of claim 7, wherein the sensors are electrodes; and
    the electrodes are directed to stimulate cells in order to trigger the impression of sight.

13. The data-compressive sensor array of claim 1, further comprising a transmitter capable of transmitting signal data provided by the decoder.

14. The data-compressive sensor array of claim 13, wherein the transmitter is a wireless transmitter.

15. The data-compressive sensor array of claim 1, further comprising a receiver capable of receiving control data.

16. The data-compressive sensor array of claim 15, wherein the receiver is a wireless receiver.

17. A method for data-compressive sensing, comprising:
    connecting a plurality of sensor circuitries in an array having a plurality of rows and a plurality of columns, where each sensor circuitry comprises:
    a sensor; and
    a comparator configured to compare a global ramp signal to a signal produced by the sensor;
    where the comparator for each sensor circuitry in a given row in the plurality of rows is connected via a given row wire;
    where the comparator for each sensor circuitry in a given column in the plurality of column is connected via a given column wire; and
    where each row wire and each column wire form a wired-OR circuit;
    sensing the state of each row wire using a row readout;
    sensing the state of each column wire using a column readout; and
    decoding the states received from the row readout and the column readout to provide signal data describing the signals produced by the sensors using a decoder implementing a pulse-position modulation scheme.

18. The method for data-compressive sensing of claim 17, wherein the plurality of sensor circuitries are implanted into the retinal ganglion cell layer of an eye.

19. The method for data-compressive sensing of claim 18, wherein the method is performed by an artificial sight prosthetic.

20. The method for data-compressive sensing of claim 18, further comprising estimating a receptive field mosaic based on the signal data.

* * * * *